(12) United States Patent  (10) Patent No.: US 8,591,668 B2
Pieroni et al.  (45) Date of Patent: Nov. 26, 2013

(54) SYSTEM FOR WASHING, STERILIZING AND PRESERVING ENDOSCOPES

(75) Inventors: Silvano Pieroni, Rome (IT); Eros De Pian, Rome (IT)

(73) Assignee: Cisa S.p.A., Rome (IT)

( * ) Notice: Subject to any disclaimer, the term of this patent is extended or adjusted under 35 U.S.C. 154(b) by 103 days.

(21) Appl. No.: 11/449,605

(22) Filed: Jun. 9, 2006

(65) Prior Publication Data

US 2006/0283483 A1  Dec. 21, 2006

(51) Int. Cl.
*B08B 9/00* (2006.01)

(52) U.S. Cl.
USPC ............... 134/166 R; 134/166 C; 134/169 C; 134/170; 134/200; 15/3; 15/300.1; 15/320; 15/322; 15/345

(58) Field of Classification Search
USPC ..... 134/166 C, 169 C, 170, 200, 166 R, 22.1, 134/22.11
See application file for complete search history.

(56) References Cited

U.S. PATENT DOCUMENTS

| | | | | |
|---|---|---|---|---|
| 4,506,544 A | * | 3/1985 | Shimizu | ............ 73/45.5 |
| 5,279,799 A | | 1/1994 | Moser | |
| 5,288,467 A | * | 2/1994 | Biermaier | .......... 422/116 |
| 5,425,815 A | * | 6/1995 | Parker et al. | ........ 134/26 |
| 5,814,009 A | * | 9/1998 | Wheatman | ............ 604/21 |
| 5,858,305 A | * | 1/1999 | Malchesky | .......... 422/28 |
| 5,882,589 A | * | 3/1999 | Mariotti | ............ 422/28 |
| 2004/0118413 A1 | * | 6/2004 | Williams et al. | .......... 128/898 |

FOREIGN PATENT DOCUMENTS

| | | |
|---|---|---|
| WO | PCT/US93/01631 | 2/1993 |
| WO | WO 93/17727 * | 9/1993 |
| WO | WO 93/17727 A | 9/1993 |

* cited by examiner

*Primary Examiner* — Eric Golightly
(74) *Attorney, Agent, or Firm* — Ladas & Parry, LLP

(57) ABSTRACT

System for washing and sterilizing endoscopes provided with multiple channels held by a sheath, comprising a machine connected by means of multiple connectors provided with safety valves to at least one case with hermetic closure into which the endoscope is positioned, in which each of the channels of the endoscope is connected by means of a connector, the inner space of the case is connected to at least one additional connector, in such a way as to inject the washing and sterilization liquids and/or the gases for emptying the channels or drying, into each of the channels of the endoscope and into the space of the case, in which the case is also provided with an outlet connector for system circulation, in which the case is detached after the working cycle of the machine and its inner space remains in sterile conditions.

13 Claims, 13 Drawing Sheets

SYSTEM FOR WASHING, STERILIZING AND PRESERVING ENDOSCOPES

SEQUENCE LISTING

Not applicable.

CROSS-REFERENCE TO RELATED APPLICATIONS

This application corresponds to Italian Patent Application No. RM2003A000570, filed on Dec. 10, 2003, and International PCT Application No. PCT/IT2004/000685, filed on Dec. 10, 2004, both of which are incorporated herein in their entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND

The invention relates to a system for washing, sterilising and preserving endoscopes.

Endoscopy is one of the medical-surgical specialisations with the greatest requirement for washing and sterilisation safety since, to perform the activity, the instrument is used on the human body and on different patients several times a day.

BRIEF SUMMARY

There is a strongly felt need to have a system for washing, sterilising and drying endoscopes that is fully automatic, has a work process of a short duration, does not damage the instruments (e.g. with high operating temperatures) is economical in use, complies with regulations, uses non hazardous substances, and allows to preserve sterility over time. Currently, in endoscopy wards, endoscopes are washed and disinfected manually or by means of apparatuses that do not provide all desired results. Hand-washing is performed by operators using special mechanical tools and detergent soaps, which allow to remove deposits from the surface of the endoscope. Once it is washed, the endoscope is disinfected by immersion in a disinfecting chemical solution, then rinsed with demineralised water before being reused.

This process offers no guarantees at all, since disinfection is not total, and there is no certainty that both the outer surface and the inner tubes are in contact with the disinfection solution. Another problem is time: obtaining a satisfactory result requires over one hour, with the consequent reduction in the use of the instrument and hence of productivity. From this follows the need to have a high number of endoscopes available and, in view of the high purchase cost, to take into account considerable depreciation with respect to the fees paid by the national health care system for each endoscopic visit. Moreover, without a protective package, it is not possible to maintain the instrument washed and disinfected until its subsequent use. This is a very important limitation for safety and use of the instruments on the human body.

A more modern and effective method for washing and disinfecting endoscopes provides for the use of apparatuses that allow to perform the operations automatically, with results that are more certain and repeatable over time.

These apparatuses are studied and built to perform automatically, on one or more endoscopes, a complete washing and disinfecting treatment, assuring a satisfactory cleanliness result and a correct level of reduction of the microbe charge. Even when using such apparatuses, it is necessary to perform some preliminary operations manually in order roughly to eliminate residues from the surface of the instruments and reduce the level of the deposits to an acceptable and constant value. The limits of the apparatuses currently available on the market relate to the fact that they do not achieve sterilisation and hence the total elimination of living forms, and they do not allow to preserve the instruments under sterile conditions.

On the market, there are several manufacturers that produce such apparatuses at different levels of quality, automation and safety such as: Wassenburg, Medivators, Olympus, Belimed. There are also apparatuses that allow only to sterilise, and preserve the endoscopes, but are not capable of washing them. The authors of the invention have provided an automatic machine for washing, disinfecting and/or sterilising, testing the integrity of, and preserving surgical instruments such as flexible endoscopes. The machine is able to complete the entire cycle in about 30 minutes at low temperatures. Moreover, the machine performs the cycle in detachable cases, suitable for stowing in cabinets, which maintain the instruments in sterile environments until use.

The machine of the invention is particularly advantageous when using cold sterilising solutions, such as the one described in EP 1.059.292. However, it is readily apparent to those skilled in the art that any cold sterilising solution can be used.

Therefore, an object of the invention is to provide a system for washing and sterilising endoscopes provided with multiple channels held by a sheath, comprising a machine connected by means of multiple connectors fitted with safety valves to at least one case with hermetic closure into which the endoscope is placed, in which each of the channels of the endoscope is connected by means of a connector, the inner space of the case is connected to at least one additional connector, in such a way as to inject the washing and sterilisation liquids and/or the gases for emptying the channels or drying, into each of the channels of the endoscope and in the space of the case, in which the case is further provided with an outlet connector for the circulation of the system, in which the case is detached after the working cycle of the machine and its inner space remains in sterile conditions.

Preferably, the machine is provided with an additional connector able to inject sterile air into the region of the endoscope inside the sheath to verify its tightness.

Preferably, the machine is connected to more than one case and it is able to perform separate cycles for each case.

An additional object of the invention is to provide a machine for washing and sterilising surgical instruments with multiple compartments provided with means for the controlled injection under pressure of washing and sterilising liquids and of drying or tightness verifying gases, into each of the compartments of the instrument to be sterilised.

A further object of the invention is to provide a case with hermetic closure for housing an endoscope, to be connected to a washing and sterilising machine, provided with one connector for each channel of the endoscope, with a further connector for the region inside the sheath of the endoscope, and with at least two additional connectors for the space of the case.

Another object of the invention is to provide a method for washing and cold sterilising endoscopes provided with multiple channels held by a sheath, in a continuous and automatic cycle comprising the steps of:
   a) conducting a tightness test on the sheath of the endoscope by injecting sterile air into the region underlying it;
   b) washing, introducing appropriate detergents at ambient temperature, into each channel of the endoscope, for appropriate time intervals;
   c) rinsing, introducing water into each channel of the endoscope;
   d) sterilising, introducing appropriate sterilising compounds at ambient temperature, into each channel of the endoscope, for appropriate time intervals;
   e) rinsing, introducing sterile water into each channel of the endoscope;
   f) drying, introducing sterile gases into each channel of the endoscope;

BRIEF DESCRIPTION OF THE SEVERAL VIEWS OF THE DRAWING

The invention shall now be described in its preferred but not limiting embodiments with reference to the following figures.

DETAILED DESCRIPTION

Figure 1:
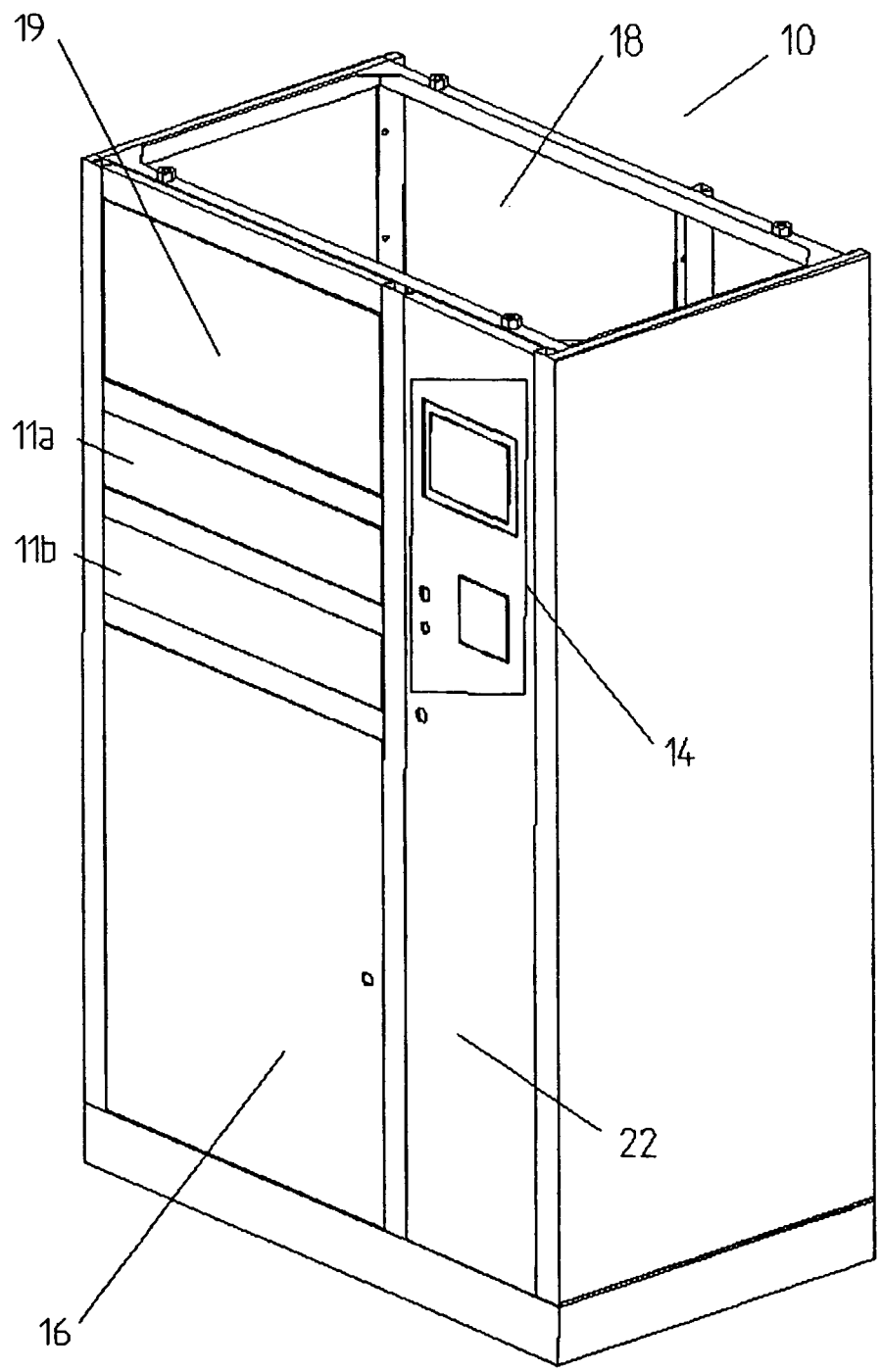
FIG. 1 is a front external perspective view of an embodiment of the machine of the invention.
Figure 1A:
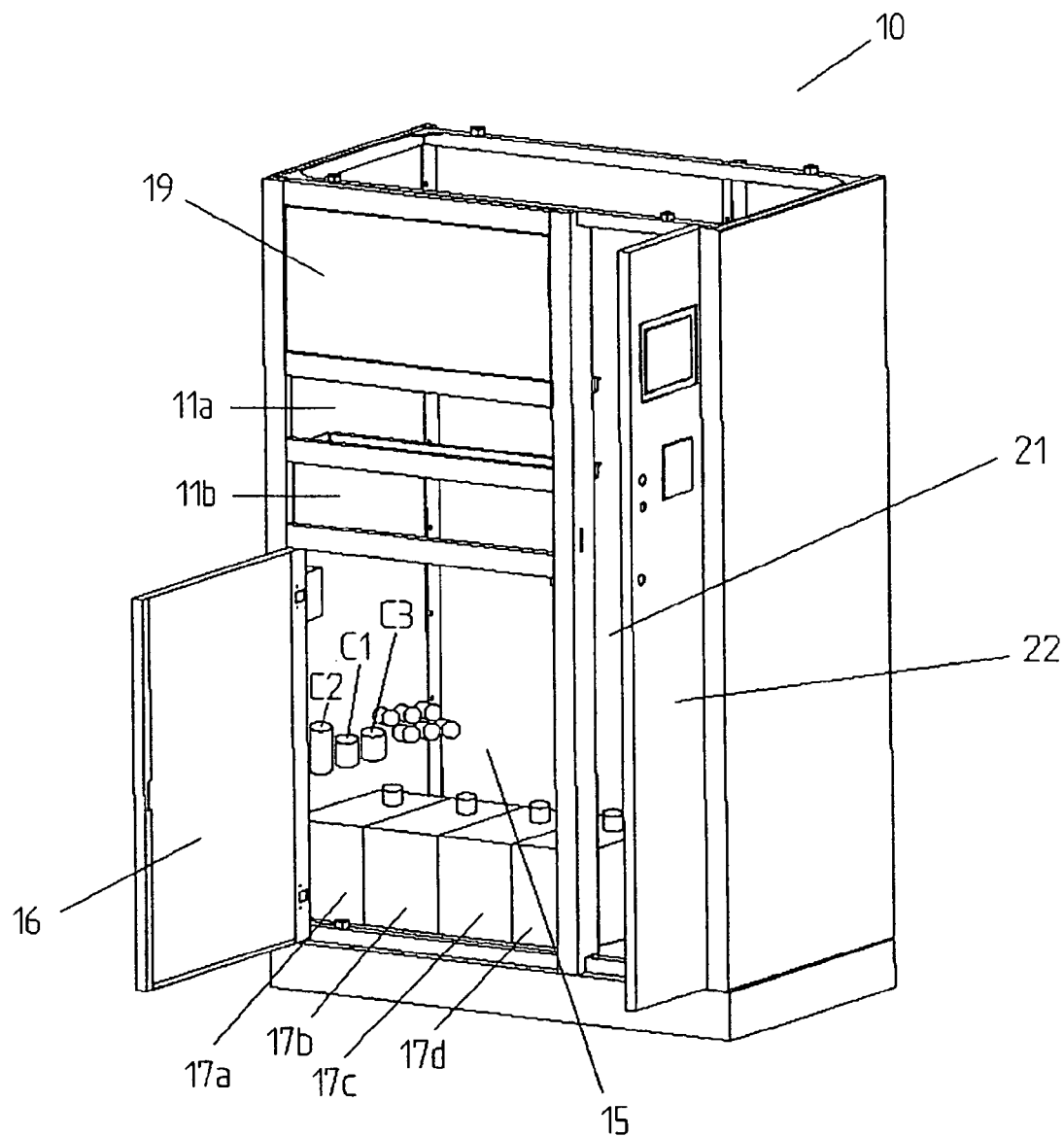
FIG. 1a is a front internal perspective view that highlights the containers of the chemical additives, the tanks and the dosing pumps.
Figure 2:
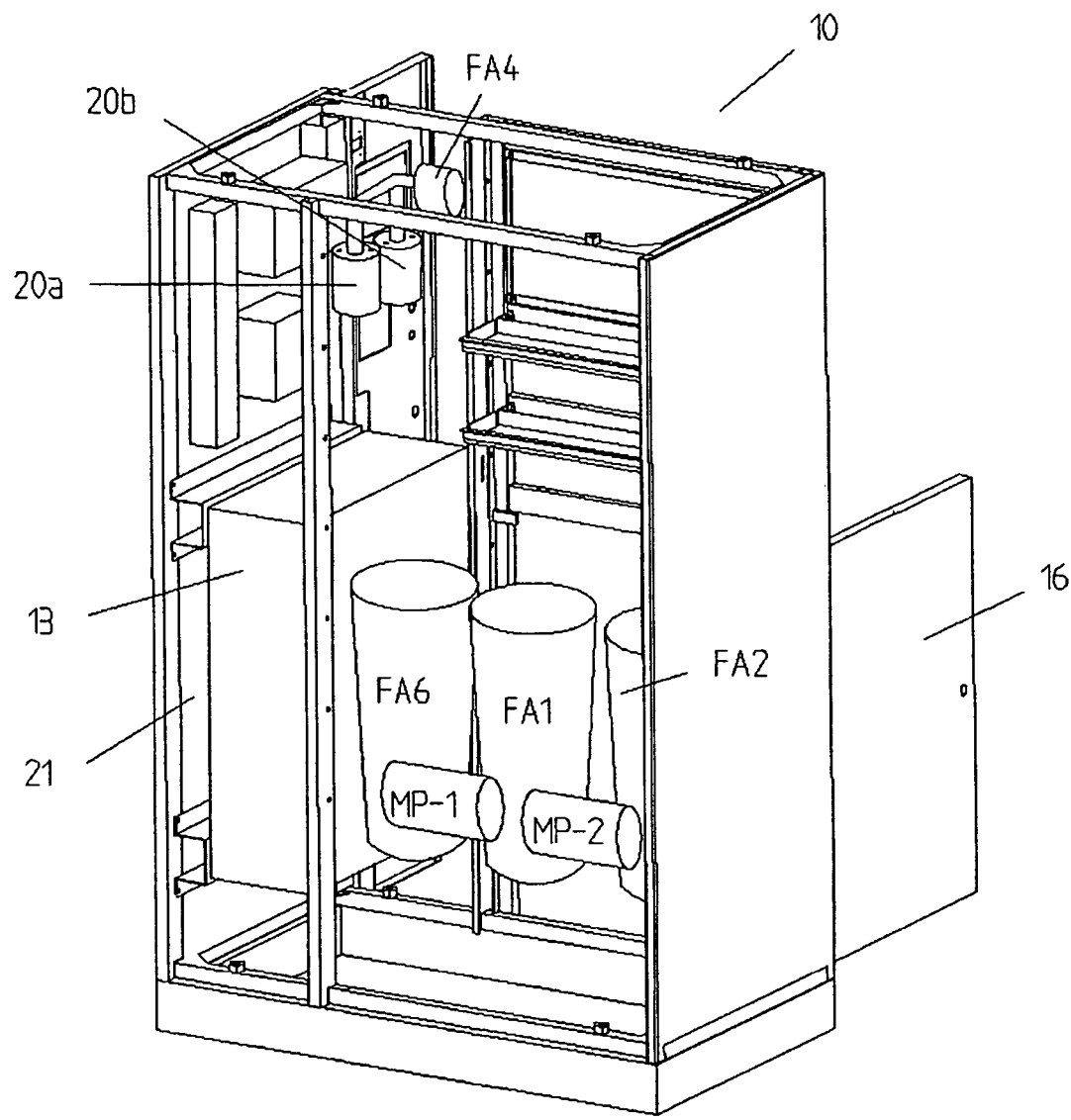
FIG. 2 is a rear internal perspective view that highlights the filters and the water pumps, the air filter and the level tanks of the water.
Figure 3:
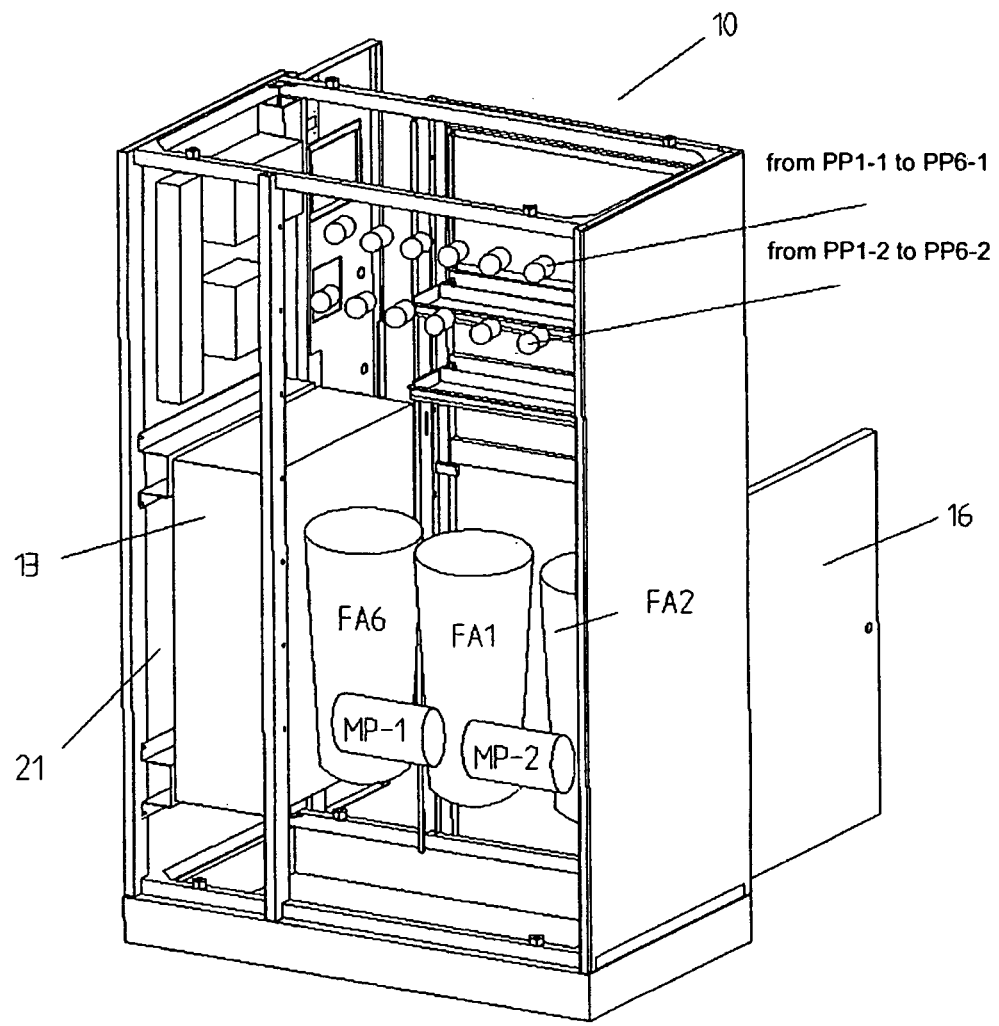
FIG. 3 is the same rear internal perspective view of FIG. 2 which highlights two series of pumps for injecting liquids into the sterilisation cases.
Figure 6:
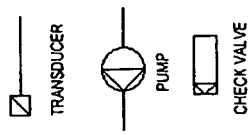
FIG. 6 is a rear view.
Figure 6:
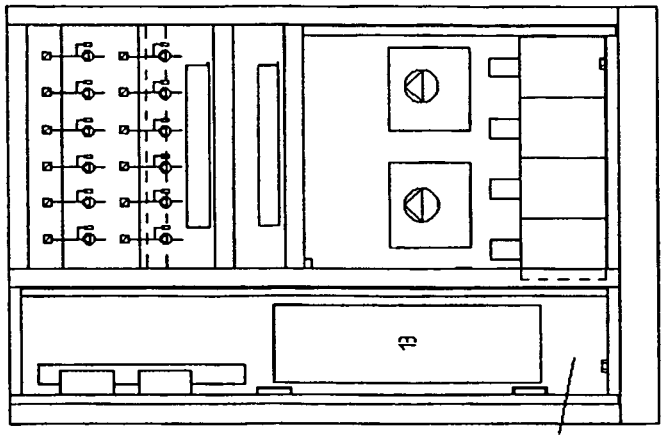
Figure 8:
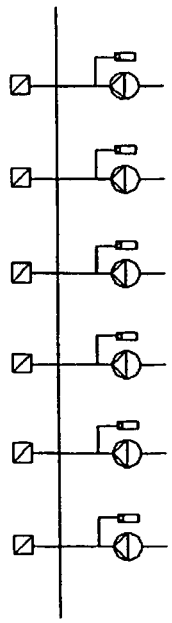
FIG. 8 is a detail of the circuit for injecting liquids and air into the sterilisation cases by means of the connectors.
Figure 5:
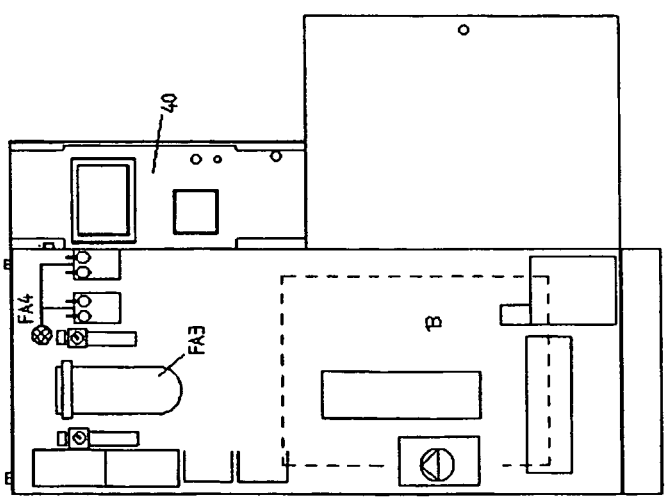
FIG. 5 is a lateral view (technical compartment side)
Figure 4:
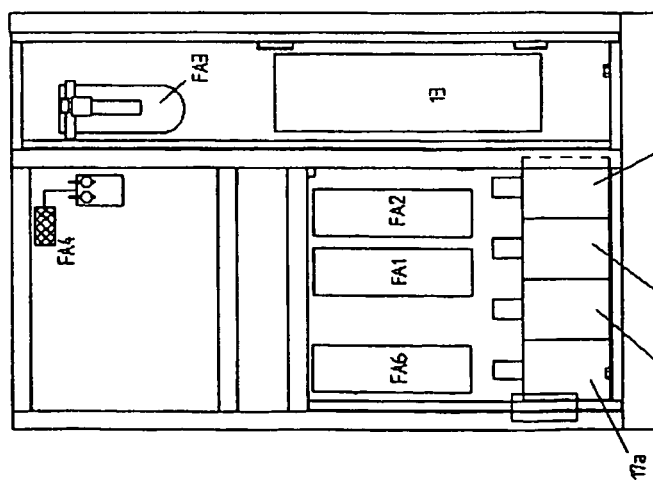
FIG. 4 is a front view.
Figure 7:
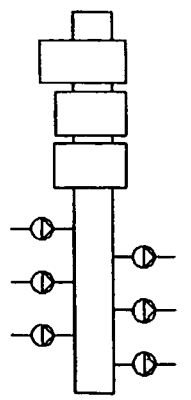
FIG. 7 is a detail of the dosing assembly of FIGS. 4 and 5.

Machine for Washing and Sterilising Endoscopes as Shown in FIGS. 1-8, and 11-12

The washing and sterilising machine 10 is provided with two compartments 11a and 11b easily accessible from the front part to allow the introduction of the cases 12 in a simple and safe manner, and to allow an easy coupling of the quick sanitary connections for connecting the channels. The compartments 11a and 11b are provided with guides to favour the sliding of the cases 12. The machine 10 is provided with a lower compartment 15 with an access door 16 for housing the containers of the liquids for washing 17a, for sterilising 17b and 17c, and for alcoholising 17d. The compartment 15 also houses the water filters FA6, FA2 and FA1 and the water pumps MP-1, MP-2, respectively for the circuits that serve the compartment 11a and 11b.

The machine 10 is also provided with an upper compartment 18 provided with door 19, which houses:
   the pumps from PP1-1 to PP6-1 for the compartment 11a and from PP1-2 to PP6-2 for the compartment 11b;
   the pressure sensors from TP1-1 to TP6-1; from TP1-2 to TP6-2;
   the check valves for compressed air from NR1-1 to NR6-1, and from NR1-2 to NR6-2;
   a compressed air filter FA3;
   an intake air filter FA4;
   two case level tanks 20a and 20b, respectively for the cases housed in the compartments 11a and 11b.

Figure 12:
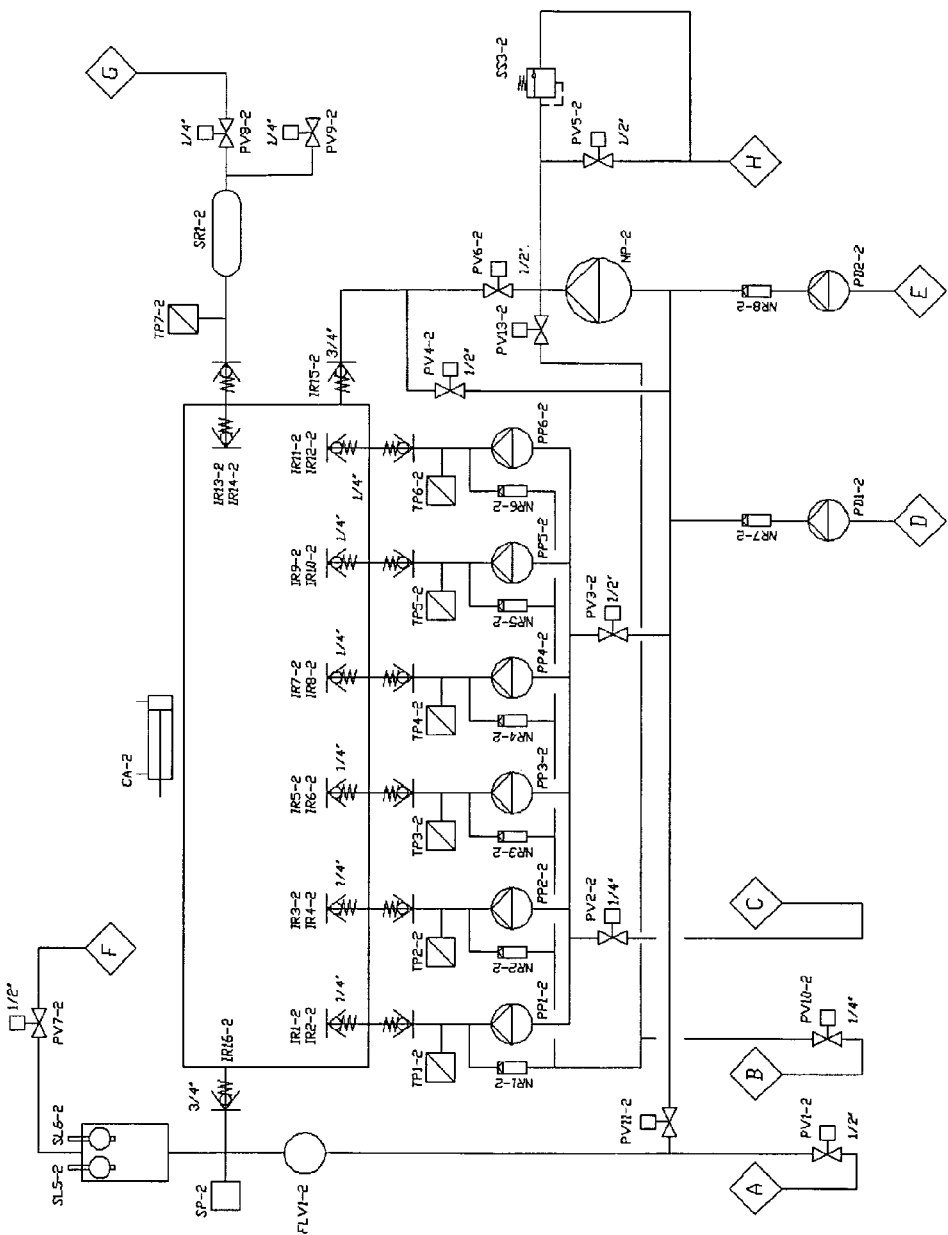
FIG. 12 shows the part of the hydraulic diagram of an embodiment of the machine according to the invention comprising the circuit dedicated to the sterilisation case 12.

Hydraulic system: it is constructed with pipelines and components (retaining valves, union fittings, etc.) of AISI 316 stainless steel. The pipelines are distinguished with conventional colours of the fluids and insulated with special silicone and Kevlar sheath to reduce thermal dispersion in the environment. All fluid inlets and the discharge are arranged in series and the connection is through flexible hoses. For each compartment 11a and 11b and hence for each case 12 a completely separate system is provided to allow treating two endoscopes at the same time. The diagram of the separate system for each case 12 is shown in FIG. 12.

Figure 11:
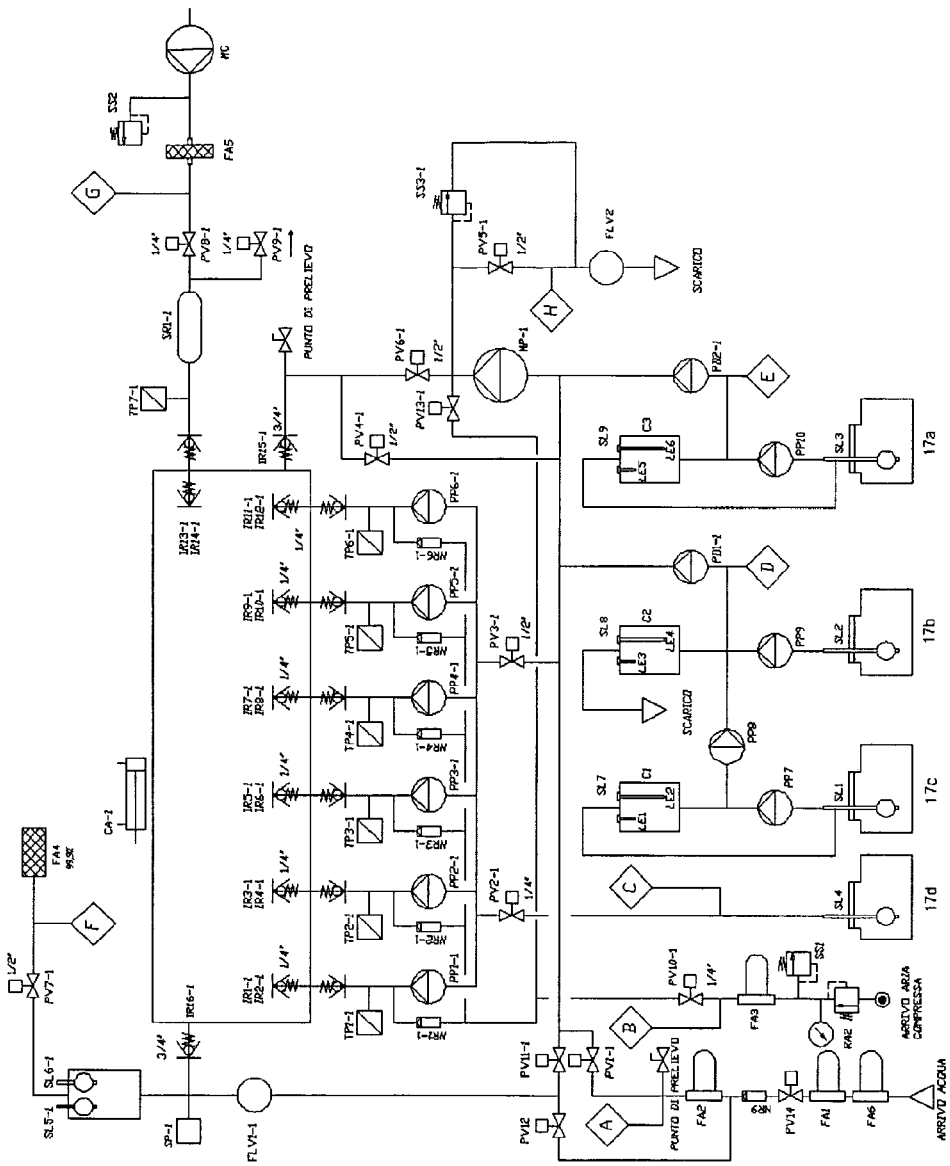
FIG. 11 shows the part of the hydraulic diagram of an embodiment of the machine according to the invention comprising the common circuit and the circuit dedicated to the sterilisation case 12.

The diagram shown in FIG. 11 shows the set of the separate system for a case 12 and of the common parts of the hydraulic circuit which are shared between the separate circuits of the cases 12. The used codes are described in the following table 1.

TABLE 1

| Code | Description | Notes |
| --- | --- | --- |
| PV1-1 | Sterile water | Electr. + valve |
| PV2-1 | Alcohol | " |
| PV3-1 | Channel Pumps H$_2$O Inlet | " |
| PV4-1 | Quick discharge | " |
| PV5-1 | Discharge | " |
| PV6-1 | Washing | " |
| PV7-1 | Battery air intake | " |
| PV8-1 | Pressure tightness test | " |
| PV9-1 | Tightness Test Vent | " |
| PV10-1 | Compressed air | " |
| PV11-1 | Water recirculation | " |
| PV12-1 | Water filter sterilisation | " |
| PV13-1 | Compressed air line sterilisation | " |

TABLE 1-continued

| Code | Description | Notes |
|---|---|---|
| MP-1 | Pump | Water pump |
| PP1-1 | Peristaltic pump 1 | Peristaltic pump |
| PP2-1 | Peristaltic pump 2 | Peristaltic pump |
| PP3-1 | Peristaltic pump 3 | Peristaltic pump |
| PP4-1 | Peristaltic pump 4 | Peristaltic pump |
| PP5-1 | Peristaltic pump 5 | Peristaltic pump |
| PP6-1 | Peristaltic pump 6 | Peristaltic pump |
| PD1-1 | Adazone dosing pump | Peristaltic pump |
| PD2-1 | Proteazone dosing pump | Peristaltic pump |
| CA-1 | Engagement cylinder | Cylinder |
| PP7 | Per. loading pump C1 | Per. Pump |
| PP8 | Per. Loading pump from C1 to C2 | " |
| PP9 | Per. Loading pump C2 | " |
| PP10 | Per. Loading pump C3 | " |
| MC | Membrane compressor | Air pump |
| TP1-1 | Peristaltic Pump Pressure Transducer 1 | 0 –2 Bar Transducer |
| TP2-1 | Peristaltic Pump Pressure Transducer 2 | 0 –2 Bar Transducer |
| TP3-1 | Peristaltic Pump Pressure Transducer 3 | 0 –2 Bar Transducer |
| TP4-1 | Peristaltic Pump Pressure Transducer 4 | 0 –2 Bar Transducer |
| TP5-1 | Peristaltic Pump Pressure Transducer 5 | 0 –2 Bar Transducer |
| TP6-1 | Peristaltic Pump Pressure Transducer 6 | 0 –2 Bar Transducer |
| TP7-1 | Tightness test pressure transducer | Transducer |
| SL5-1 | Water level | Level sensor |
| SL6-1 | Water level | Level sensor |
| SP-1 | Pump manostat | Manostat |
| SQ1-1 | Inserted drawer end stop | End stop |
| SL1 | Additive 1 level (per acetic A.) | Asp. nozzle + sens. |
| SL2 | Additive 2 level (Adazone) | " |
| SL3 | Additive 3 level (Proteazone) | " |
| SL4 | Additive 4 level (alcohol) | " |
| LE1 | Electronic level probe | |
| LE2 | Electronic level probe | |
| LE3 | Electronic level probe | |
| LE4 | Electronic level probe | |
| LE5 | Electronic level probe | |
| LE6 | Electronic level probe | |
| FA1 | 0.45 water pre-filter | |
| FA2 | 0.2 water filter | |
| FA3 | 0.2 compressed air filter | |
| FA4 | 0.2 intake filter | |
| FA5 | Test compressed air filter | |
| FA6 | 1.00 water pre-filter | |
| NR1-1 to NR6-1 | Channel compressed air check valve | |
| NR9 | Water line check valve | |
| IR1-1 to IR16-1 | Container quick coupling fittings | |
| SR1-1 | Test compressed air tank | |
| FLV1-1 | Chamber flow regulator | |
| FLV2 | Discharge flow regulator | |
| SS1 | Compressed air safety valve | |
| SS2 | Test compressed air safety valve | |
| SS3-1 | Water loop safety valve | |
| RA2 | Compressed air reducer | |

The points A, B, C, D, E, F, G and H shown in FIGS. 11 and 12 are the connecting points between the two hydraulic diagrams.

The machine 10 is adapted to be connected and hence use cold water and compressed air. The water loop has a system NR9 which prevents the water from flowing back and hence the risk of pollution in the line. The water, flowing into the machine 10, is filtered by means of 10 the filters FA6, FA1 and FA2 arranged in series. A loop is provided for sterilising the filter FA2 through the valve PV12. Also provided is a device for safely controlling the level of the water SL5-1, SL6-1 for the case housed in the compartment 11*a*, and SL5-2, SL6-2 for the one housed in the compartment 11*b*, to allow its automatic loading in sufficient quantities to assure its correct and total filling. For each inlet channels of the liquids of the case 12 are provided the pumps PP1-1, PP2-1, PP3-1, PP4-1, PP5-1, PP6-1, (compartment 11*a*) and PP1-2, PP2-2, PP3-2, PP4-2, PP5-2, PP6-2 (compartment 11*b*), appropriately dimensioned, complete with related devices TP1-1, TP2-1, TP3-1, TP4-1, TP5-1, TP6-1 and TP1-2, TP2-2, TP3-2, TP4-2, TP5-2, TP6-2 for safely controlling their functionality, which circulate the liquids in constant and continuous fashion to assure contact with the interior and exterior surface of the channels of the endoscope.

The liquids are discharged by means of the same pumps as the inlet channels of the liquids, in such a way as to assure their complete elimination.

Electrical System:

it is built inside the machine and in compliance with current applicable European and Italian regulations. All electrical components, with the exception of command and control components, which are conveniently located in the front, are mounted connected to a terminal board and enclosed in an electrical panel 13 with degree of protection IP55 which in turn is positioned inside the apparatus 10, in a compartment 21 provided with door 22.

The control panel 14 is installed on the front of the apparatus 10, has an internal degree of protection IP54 and external degree of protection IP22 and provides all components for its command and control.

Drying Device:

a final drying step is provided with the removal of the residual water drops. A unit operating with sterile compressed air and complete with filter FA3 allows to eliminate the residual drops present in the channels of the endoscope and inside the case 12. A safety device SS1 protects the instruments against overpressures.

Dosing Device:

The chemical additives which favour the washing and sterilising of the instruments are added to the water by means of four dosing pumps PD1-1, PD2-1, PD1-2 and PD2-2 which draw the liquid directly from the tanks C2 and C3.

The very low delivery of the dosing pumps PD1-1, PD2-1 and PD1-2, PD2-2 and the control of the dosage by means of the measuring devices LE1, LE2, LE3, LE4, LE5 and LE6 of the tanks C1, C2 and C3, allow to optimise the quantities of additives added to the water and to reduce their consumption. A level control SL1, SL2, SL3 and SL4 is provided for each container 17*a*, 17*b*, 17*c* and 17*d* of chemical additives and the presence of additive is indicated until the container is completely emptied. The additive is injected into the circuit gradually and it enters the case 12 already mixed to prevent it from coming in contact with the instrument yet concentrated. The additives which are added are: detergent, steriliser (adazone+peracetic acid) and alcohol.

Safety Device:

The machine 10 is provided with safety devices which make it extremely reliable, such as:

- device against the extraction of the case 12 during the execution of the cycle;
- device for controlling the overpressure of compressed air SS1 and SS2 and of water SS3-1 and SS3-2;
- device against the injection of water into the case 12 if the connection with the couplings did not take place;
- magneto-thermal breakers to protect the motors;
- fuse and electric protection on the auxiliaries of the electrical system;
- short circuit and overheating protection (magneto-thermal breaker);
- emergency mushroom head push-button for arresting all functions of the machine (returning to stand-by with the rotation of said push-button and restarting the cycle functionality with a new start command);
- disengagement micro-switches on the electrical power panel;
- emergency push-button positioned on the control panel for immediately arresting the operation;

Management System:

The machine 10 is fully controlled with programmable logic electronic systems which allow to manage the cycles, control the parameters and verify process safeties. The management system has the following characteristics:

- absolute simplicity and clarity in the information provided, both on monitor and on printer, without use of codes but with clear messages, thanks to the use of a "touch-screen" interactive system, thus requiring no personnel with machine language knowledge;
- the programs required for washing are inserted in stable memories (EEPROM) in the machine at the time of delivery and therefore are indelible;
- standard cycles are selectable from the "touch-screen", selecting the cycles page on the menu; the cycles page shows the push-buttons of the executable cycles and, once the one for the selected cycle is pressed, starting authorisation is given, after confirming by pressing START; however new cycles can be programmed through the keyboard by setting their parameters;
- the control system is provided with help pages which guide the operator, step by step, to use and learn the standard cycles and the new cycles. Access to the programming of new cycles requires knowledge of an "access key".

Description of the Control Device:

The system comprises two devices, one (PLC) for controlling and the other one for verifying functionality and safety (W.D.). The two devices are installed aboard the machine inside the electrical panel 13. A third operator interface device is installed on the control panel 14.

The basic apparatus is constituted by a programmable electronic controller, comprising:

- power supply device, appropriately dimensioned for any subsequent expansions of the control boards;
- PCU board with 7.2K of program memory and 6 K of data memory with 1.0 ms watchdog time;
- memory card, complete with 8 KWORD EEPROM memory;
- capability for remote connection with an external memory (RS232C serial output);
- control boards, each for 16 digital outputs and 16 digital inputs, with connector connection, and for 4 analogue inputs 4-20 mA and 2 analogue outputs 4-20 mA;
- data BACKUP battery, with a 10-year duration.

Apparatus Regulation System:

Managed by a programmable electronic controller, which in turn is verified for its integrity by an external device to have a confirmation on the correct performance of the cycle (W.D.).

The controller manages the recording of the data on the printer.

The process control system receives analogue signals from the measuring sensors and reports the value displayed on the "touch-screen" with real time updates.

The system is capable of self-diagnosis.

Programs can be freely set by the user through the "touch-screen" and, after a program is completely set, it can be executed automatically and remain available for repeated calls for execution. A 24 column alphanumeric printer records the documentation of the messages, of the parameters and of the regular performance of the cycles.

Safety and alarm systems of the programmable electronic controller are also provided at different levels, e.g.:

- indications which intervene during the execution of the cycle, before or after the cycle, but do not modify the execution of the cycle;
- indications of alarm for non severe anomalies, with visual and acoustic signal, which recall the operator's attention, but without intervening in the execution of the cycle;
- indications of alarm with visual and acoustic signal which intervene for sever anomalies and which modify the behaviour of the cycle even so far as to block it.

Case

Figure 9:
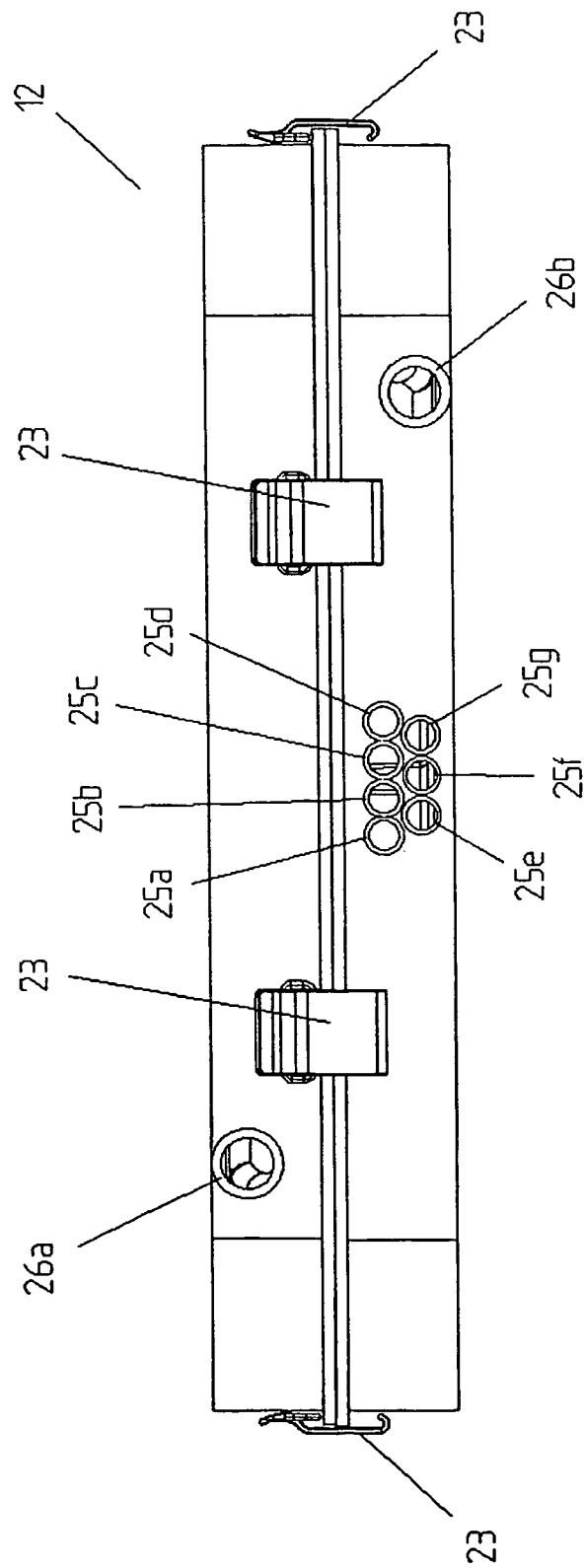
FIG. 9 is a rear view of the sterilisation case 12 which highlights the connectors.
Figure 10:
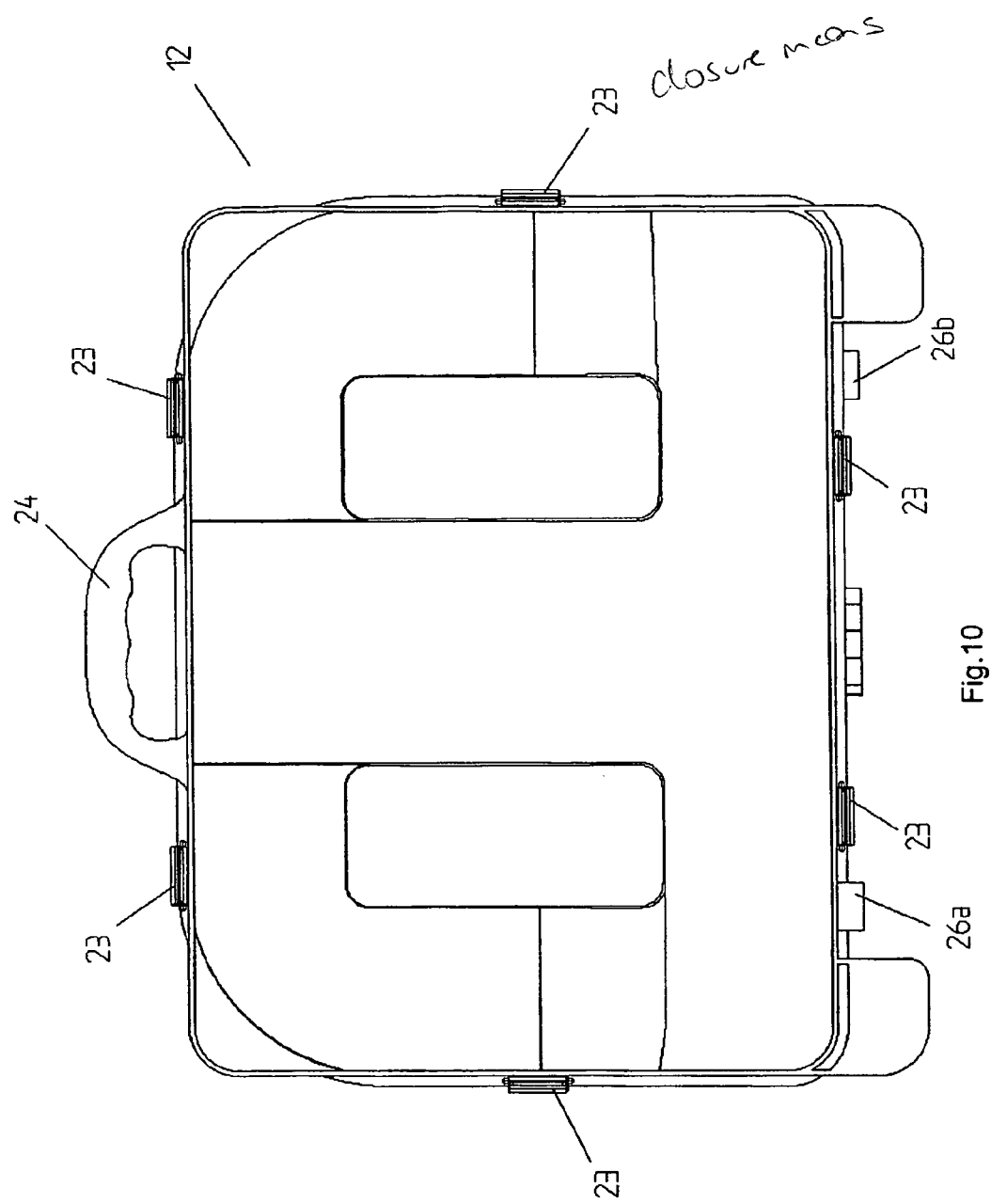
FIG. 10 is a top view of the sterilisation case 12.

As shown in FIGS. 9 to 10, the case 12 is built to assure the effectiveness of the treatment of the instrument and its preservation in a sterile environment. For this reason it has the following requirements: it is made of plastic material; it is light, strong and non deformable; it can be drained perfectly; its inner surface is rounded and smooth; it is compatible with its intended use; it has a sanitary construction; it is resistant to the substances used for the treatment; it has an inner shape that is suitable to house all the endoscopes by the different manufacturers; it is hermetically sealed by means of closures 23; its inner space is right for the endoscope and its capacity in liters is minimal; it is easily transportable with a handle 24; it has a display where the data of the content can be shown; it has the capability of maintaining the content sterile; it has quick couplings for connection to the washing and sterilising machine, 25*a-f* for the channels of the endoscope, 25*g* for the tightness test, and 26*a* and 26*b* for injecting and discharging the liquid in the inner space of the case 12.

Drying Cabinet

The drying cabinet has the function of drying the endoscope and preserving it in a sterile environment. Drying is achieved by safely heating the air that is injected into the channels of the endoscope inside the case by means of the connectors.

Work Cycle

The sequence of the various steps of the cycle is subordinated to the achievement of the specified conditions and of the set parameters. The steps are as follows:

Tightness Test:

Injection of compressed air into the sheath of the endoscope by means of the air pump MC and test of the pressure drop by means of pressure sensor TP7-1 and TP7-2. The injected air is filtered by the filter FA5.

Washing:

Injection of the detergent into the dosage tank C3 through the pump PP10 with dosage control through the measuring devices LE5 and LE6; loading the sterile water with the related detergent into the case 12 by means of the pumps MP-1, PD2-1 and MP-2, PD2-2; forced washing with the circulation pumps PP1-1, PP2-1, PP3-1, PP4-1, PP5-1, PP6-1 and PP1-2, PP2-2, PP3-2, PP4-2, PP5-2, PP6-2 for a time interval that depends on the detergent in use; discharge of the solution through the discharge valve PV5-1, PV5-2 and cleaning of the channels with compressed air filtered by the filter FA3.

Rinsing:

Loading sterile air into the case 12 by means of the pumps MP-1 and MP-2; forced rinsing with circulation pumps PP1-1, PP2-1, PP3-1, PP4-1, PP5-1, PP6-1 and PP1-2, PP2-2, PP3-2, PP4-2, PP5-2, PP6-2; discharging through the discharge valve PV5-1, PV5-2 and cleaning the channels with compressed air filtered by the filter FA3.

Sterilisation:

Preparation of the dosage of the peracetic acid and adazone (or of another sterilising compound) according to the following steps:

injection of the peracetic acid into the dosage tank C1 by means of the pump PP7, with dosage control by means of the measuring devices LE1 and LE2;

transferring the content of the dosage tank C1 into the dosage tank C2 by means of the pump PP8;

injection of the adazone into the dosage tank C2 by means of the pump PP9, with dosage control by means of the measuring devices LE3 and LE4;

loading sterile water with the related sterilising compound into the case 12 by means of the pumps MP-1, PD1-1 and MP-2, PD1-2; forced washing with the circulation pumps PP1-1, PP2-1, PP3-1, PP4-1, PP5-1, PP6-1 and PP1-2, PP2-2, PP3-2, PP4-2, PP5-2, PP6-2 for a time interval from 10 minutes to 40 minutes, variable according to the sterilising compound in use (sterilisation); discharge of the solution through the discharge valve PV5-1, PV5-2 and cleaning the channels with compressed air filtered by means of the filter FA3.

Rinsing:

Loading sterile water into the case 12 by means of the pump MP-1 and MP-2; forced rinsing with circulation pumps PP1-1, PP2-1, PP3-1, PP4-1, PP5-1, PP6-1 and PP1-2, PP2-2, PP3-2, PP4-2, PP5-2, PP6-2; discharge of the solution through the discharge valve PV5-1, PV5-2 and cleaning the channels with compressed air filtered by means of the filter FA3.

Alcoholisation:

Injection of alcohol into the channels through valve PV2-1 and PV2-2 by means of the pumps PP1-1, PP2-1, PP3-1, PP4-1, PP5-1, PP6-1 and PP1-2, PP2-2, PP3-2, PP4-2, PP5-2, PP6-2; injection of compressed air filtered by means of the filter FA3 into the channel and dilution of the alcohol; discharge of the residual solution.

Drying:

Drying takes place at the end of the cycle, preferably with injection of sterile air into the case and into the channels, but it can also be conducted subsequently in proper drying cabinet.

Description of the Apparatuses Machine for Washing and Sterilising Endoscopes as Shown in FIGS. 1-8, and 16-17

The washing and sterilising machine 10 is provided with two compartments 11a and 11b easily accessible from the front part to allow the introduction of the cases 28 in a simple and safe manner, and to allow an easy coupling of the quick sanitary connections for connecting the channels. The compartments 11a and 11b are provided with guides to favour the sliding of the cases 28. The machine 10 is provided with a lower compartment 15 with an access door 16 for housing the containers of the liquids for washing 17a, for sterilising 17b and 17c, and for alcoholising 17d. The compartment 15 also houses the water filters FA6, FA2 and FA1 and the water pumps MP-1, MP-2, respectively for the circuits that serve the compartment 11a and 11b.

The machine 10 is also provided with an upper compartment 18 provided with door 19, which houses: the pumps from PP1-1 to PP6-1 for the compartment 11a and from PP1-2 to PP6-2 for the compartment 11b;

the pressure sensors from TP1-1 to TP6-1; from TP1-2 to TP6-2;

the check valves for compressed air from NR1-1 to NR6-1, and from NR1-2 to NR6-2;

a compressed air filter FA3;

an intake air filter FA4;

two case level tanks 20a and 20b, respectively for the cases housed in the compartments 11a and 11b.

Figure 17:
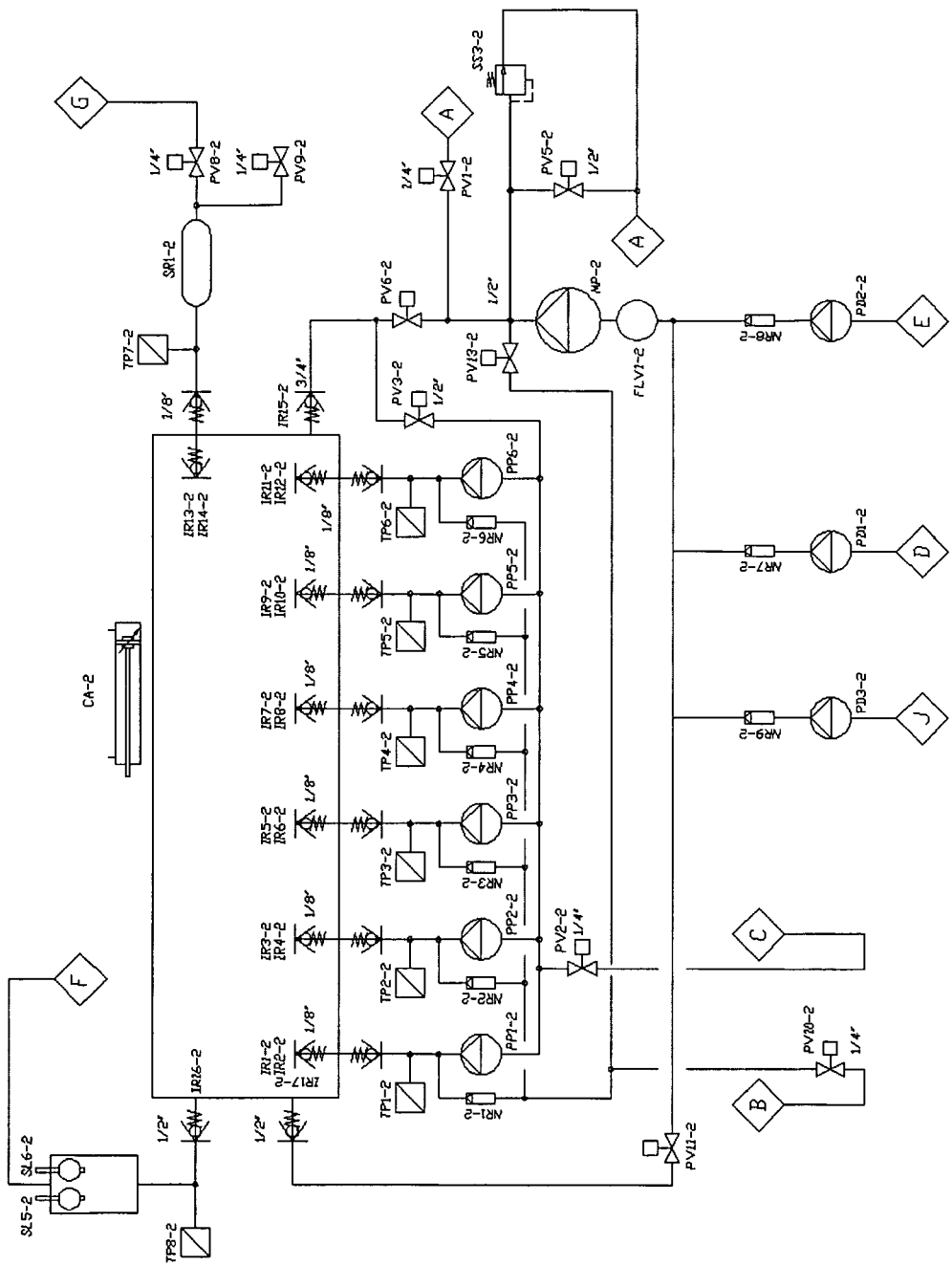
FIG. 17 shows the part of the hydraulic diagram of an embodiment of the machine according to the invention comprising the circuit dedicated to the sterilisation case 28.

Hydraulic System:

It is constructed with pipelines and components (retaining valves, union fittings, etc.) of AISI 316 stainless steel. The pipelines are distinguished with conventional colours of the fluids and insulated with special silicone and Kevlar sheath to reduce thermal dispersion in the environment. All fluid inlets and the discharge are arranged in series and the connection is through flexible hoses. For each compartment 11a and 11b and hence for each case 28 a completely separate system is provided to allow treating two endoscopes at the same time. The diagram of the separate system for each case 28 is shown in FIG. 17.

Figure 16:
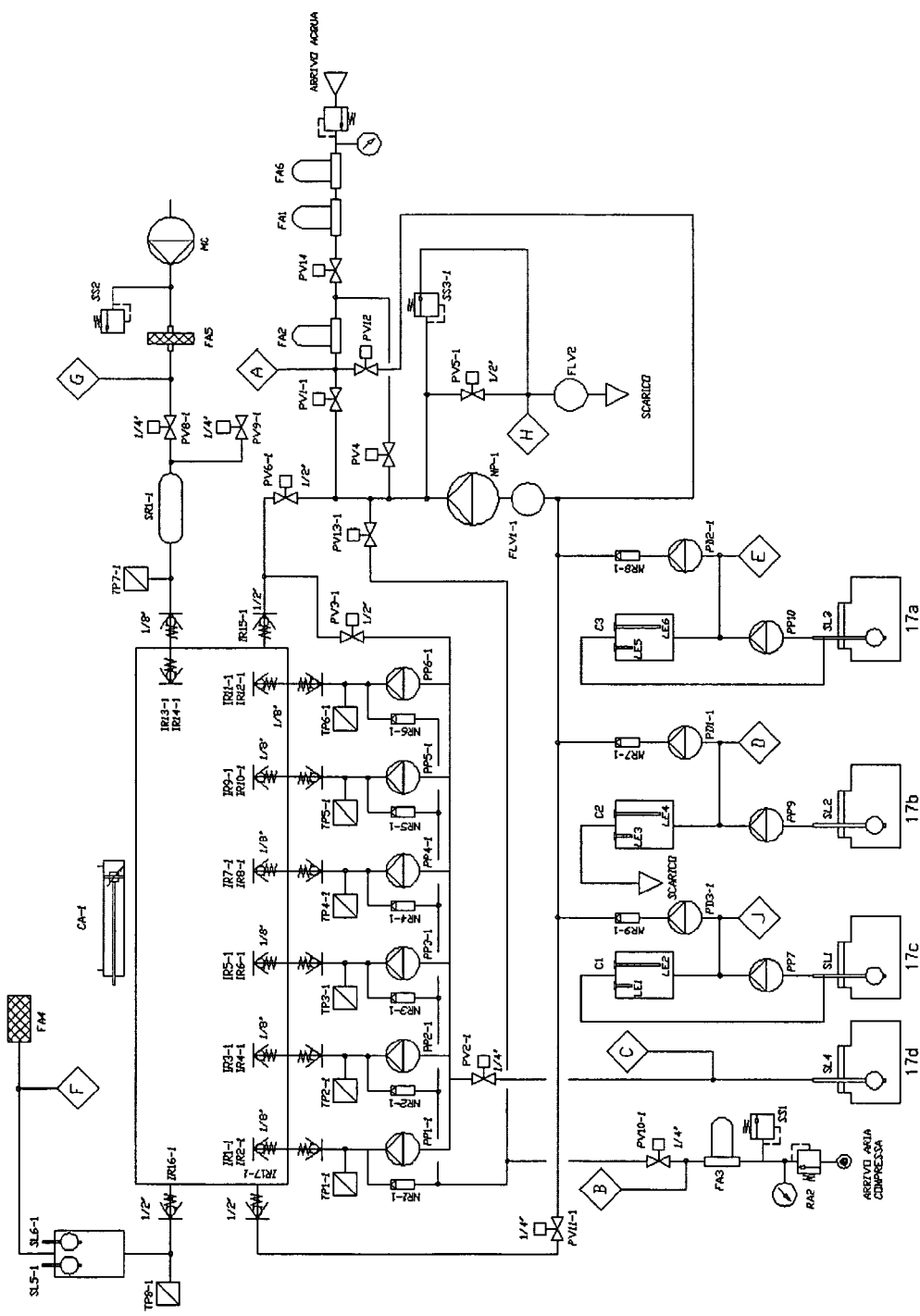
FIG. 16 shows the part of the hydraulic diagram of an embodiment of the machine according to the invention comprising the common circuit and the circuit dedicated to the sterilisation case 28.

The diagram shown in FIG. 16 shows the set of the separate system for a case 28 and of the common parts of the hydraulic circuit which are shared between the separate circuits of the cases 28. The used codes are described in the following table 2.

TABLE 2

| Code | Description | Notes |
| --- | --- | --- |
| PV1-1 | Sterile water | Electr. + valve |
| PV2-1 | Alcohol | " |
| PV3-1 | Channel Pumps H$_2$O Inlet | " |
| PV4 | Sterilisation filter H$_2$O Inlet | " |
| PV5-1 | Discharge | " |
| PV6-1 | Washing | " |
| PV8-1 | Pressure tightness test | " |
| PV9-1 | Tightness Test Vent | " |
| PV10-1 | Compressed air | " |
| PV11-1 | Water recirculation | " |
| PV12 | Sterilisation filter H$_2$O Outlet | " |
| PV13-1 | Compressed air line sterilisation | " |
| PV14 | H$_2$O Inlet | " |
| MP-1 | Pump | Water pump |
| PP1-1 | Peristaltic pump 1 | Peristaltic pump |
| PP2-1 | Peristaltic pump 2 | Peristaltic pump |
| PP3-1 | Peristaltic pump 3 | Peristaltic pump |
| PP4-1 | Peristaltic pump 4 | Peristaltic pump |
| PP5-1 | Peristaltic pump 5 | Peristaltic pump |
| PP6-1 | Peristaltic pump 6 | Peristaltic pump |
| PD1-1 | Adaz. dosing pump | Peristaltic pump |
| PD2-1 | Proteazone dosing pump | Peristaltic pump |
| PD3-1 | Peracetic A. dosing pump | Peristaltic pump |

TABLE 2-continued

| Code | Description | Notes |
|---|---|---|
| CA-1 | Engagement cylinder | Cylinder |
| PP7 | Per. loading pump C1 | Per. Pump |
| PP9 | Per. Loading pump C2 | " |
| PP10 | Per. Loading pump C3 | " |
| MC | Membrane compressor | Air pump |
| TP1-1 | Peristaltic Transducer 1 | 0 –2 Bar Transducer |
| TP2-1 | Peristaltic Transducer 2 | 0 –2 Bar Transducer |
| TP3-1 | Peristaltic Transducer 3 | 0 –2 Bar Transducer |
| TP4-1 | Peristaltic Transducer 4 | 0 –2 Bar Transducer |
| TP5-1 | Peristaltic Transducer 5 | 0 –2 Bar Transducer |
| TP6-1 | Peristaltic Transducer 6 | 0 –2 Bar Transducer |
| TP7-1 | Tightness test pressure transducer | Transducer |
| TP8-1 | Pump pressure transducer | Transducer |
| SL5-1 | Water level | Level sensor |
| SL6-1 | Water level | Level sensor |
| SQ1-1 | Inserted drawer end stop | End stop |
| SL1 | Additive 1 level (per acetic A.) | Asp. nozzle + sens. |
| SL2 | Additive 2 level (Adazone) | " |
| SL3 | Additive 3 level (Proteazone) | " |
| SL4 | Additive 4 level (alcohol) | " |
| LE1 | Electronic level probe | |
| LE2 | Electronic level probe | |
| LE3 | Electronic level probe | |
| LE4 | Electronic level probe | |
| LE5 | Electronic level probe | |
| LE6 | Electronic level probe | |
| FA1 | 0.45 water pre-filter | |
| FA2 | 0.2 water filter | |
| FA3 | 0.2 compressed air filter | |
| FA4 | 0.2 intake filter | |
| FA5 | Test compressed air filter | |
| FA6 | 1.00 water pre-filter | |
| NR1-1 to NR6-1 | Channel compressed air check valve | |
| NR7-1 | Adazone check valve | |
| NR8-1 | Proteazone check valve | |
| NR9-1 | Perecetic A. check valve | |
| IR1-1 to IR17-1 | Container quick coupling fittings | |
| SR1-1 | Test compressed air tank | |
| FLV1-1 | Chamber flow regulator | |
| FLV2 | Discharge flow regulator | |
| SS1 | Compressed air safety valve | |
| SS2 | Test compressed air safety valve | |
| SS3-1 | Water loop safety valve | |
| RA2 | Compressed air reducer | |

The points A, B, C, D, E, F, G, H and J shown in FIGS. 16 and 17 are the connecting points between the two hydraulic diagrams.

The machine 10 is adapted to be connected and hence use cold water and compressed air. The water, flowing into the machine 10, is filtered by means of the filters FA6, FA1 and FA2 arranged in series. A loop is provided for sterilising the filter FA2 through the valve PV4 and PV12. Also provided is a device for safely controlling the level of the water SL5-1, SL6-1 for the case housed in the compartment 11a, and SL5-2, SL6-2 for the one housed in the compartment 11b, to allow its automatic loading in sufficient quantities to assure its correct and total filling. For each inlet channels of the liquids of the case 28 are provided the pumps PP1-1, PP2-1, PP3-1, PP4-1, PP5-1, PP6-1, (compartment 11a) and PP1-2, PP2-2, PP3-2, PP4-2, PP5-2, PP6-2 (compartment 11b), appropriately dimensioned, complete with related devices TP1-1, TP2-1, TP3-1, TP4-1, TP5-1, TP6-1 and TP1-2, TP2-2, TP3-2, TP4-2, TP5-2, TP6-2 for safely controlling their functionality, which circulate the liquids in constant and continuous fashion to assure contact with the interior and exterior surface of the channels of the endoscope.

The liquids are discharged by means of the same pumps as the inlet channels of the liquids, in such a way as to assure their complete elimination.

Electrical System:

It is built inside the machine and in compliance with current applicable European and Italian regulations. All electrical components, with the exception of command and control components, which are conveniently located in the front, are mounted connected to a terminal board and enclosed in an electrical panel 13 with degree of protection IP55 which in turn is positioned inside the apparatus 10, in a compartment 21 provided with door 22.

The control panel 14 is installed on the front of the apparatus 10, has an internal degree of protection IP54 and external degree of protection IP22 and provides all components for its command and control.

Drying Device:

A final drying step is provided with the removal of the residual water drops. A unit operating with sterile compressed air and complete with filter FA3 allows to eliminate the residual drops present in the channels of the endoscope and inside the case 28. A safety device SS1 protects the instruments against overpressures.

Dosing Device:

The chemical additives which favour the washing and sterilising of the instruments are added to the water by means of six dosing pumps PD1-1, PD2-1, PD3-1, PD1-2, PD2-2 and PD3-2 which draw the liquid directly from the tanks C1, C2 and C3.

The very low delivery of the dosing pumps PD1-1, PD2-1, PD3-1 and PD1-2, PD2-2, PD3-2 and the control of the dosage by means of the measuring devices LE1, LE2, LE3, LE4, LE5 and LE6 of the tanks C1, C2 and C3, allow to optimise the quantities of additives added to the water and to reduce their consumption. A level control SL1, SL2, SL3 and SL4 is provided for each container 17a, 17b, 17c and 17d of chemical additives and the presence of additive is indicated until the container is completely emptied. The additive is injected into the circuit gradually and it enters the case 28 already mixed to prevent it from coming in contact with the instrument yet concentrated. The additives which are added are: detergent, steriliser (adazone+peracetic acid) and alcohol.

Safety Device:

The machine 10 is provided with safety devices which make it extremely reliable, such as:
 device against the extraction of the case 28 during the execution of the cycle;
 device for controlling the overpressure of compressed air SS1 and SS2 and of water SS3-1 and SS3-2;
 device against the injection of water into the case 28 if the connection with the couplings did not take place;
 magneto-thermal breakers to protect the motors;
 fuse and electric protection on the auxiliaries of the electrical system;
 short circuit and overheating protection (magneto-thermal breaker);
 emergency mushroom head push-button for arresting all functions of the machine (returning to stand-by with the rotation of said push-button and restarting the cycle functionality with a new start command);

disengagement micro-switches on the electrical power panel;

emergency push-button positioned on the control panel for immediately arresting the operation;

Management System:

The machine 10 is fully controlled with programmable logic electronic systems which allow to manage the cycles, control the parameters and verify process safeties. The management system has the following characteristics:

absolute simplicity and clarity in the information provided, both on monitor and on printer, without use of codes but with clear messages, thanks to the use of a "touch-screen" interactive system, thus requiring no personnel with machine language knowledge;

the programs required for washing are inserted in stable memories (EEPROM) in the machine at the time of delivery and therefore are indelible;

standard cycles are selectable from the "touch-screen", selecting the cycles page on the menu; the cycles page shows the push-buttons of the executable cycles and, once the one for the selected cycle is pressed, starting authorisation is given, after confirming by pressing START; however new cycles can be programmed through the keyboard by setting their parameters;

the control system is provided with help pages which guide the operator, step by step, to use and learn the standard cycles and the new cycles. Access to the programming of new cycles requires knowledge of an "access key".

Description of the Control Device:

The system comprises two devices, one (PLC) for controlling and the other one for verifying functionality and safety (W.D.). The two devices are installed aboard the machine inside the electrical panel 13. A third operator interface device is installed on the control panel 14.

The basic apparatus is constituted by a programmable electronic controller, comprising:

power supply device, appropriately dimensioned for any subsequent expansions of the control boards;

PCU board with 7.2K of program memory and 6 K of data memory with 1.0 ms watchdog time;

memory card, complete with 8 KWORD EEPROM memory;

capability for remote connection with an external memory (RS232C serial output);

control boards, each for 16 digital outputs and 16 digital inputs, with connector connection, and for 4 analogue inputs 4-20 mA and 2 analogue outputs 4-20 mA;

data BACKUP battery, with a 10-year duration.

Apparatus Regulation System:

Managed by a programmable electronic controller, which in turn is verified for its integrity by an external device to have a confirmation on the correct performance of the cycle (W.D.).

The controller manages the recording of the data on the printer.

The process control system receives analogue signals from the measuring sensors and reports the value displayed on the "touch-screen" with real time updates. The system is capable of self-diagnosis.

Programs can be freely set by the user through the "touch-screen" and, after a program is completely set, it can be executed automatically and remain available for repeated calls for execution. A 24 column alphanumeric printer records the documentation of the messages, of the parameters and of the regular performance of the cycles.

Safety and alarm systems of the programmable electronic controller are also provided at different levels, e.g.:

indications which intervene during the execution of the cycle, before or after the cycle, but do not modify the execution of the cycle;

indications of alarm for non severe anomalies, with visual and acoustic signal, which recall the operator's attention, but without intervening in the execution of the cycle;

indications of alarm with visual and acoustic signal which intervene for sever anomalies and which modify the behaviour of the cycle even so far as to block it.

Case

Figure 13:
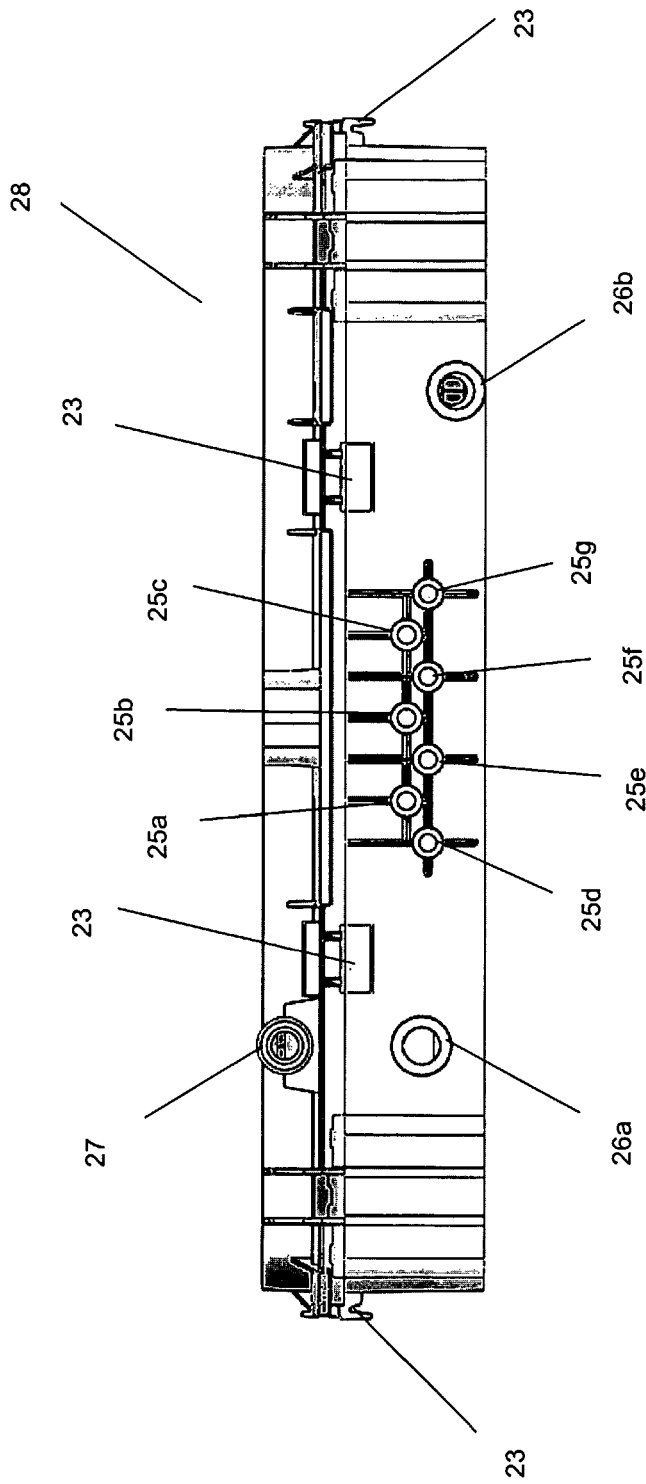
FIG. 13 is a rear view of the sterilisation case 28 which highlights the connectors.
Figure 14:
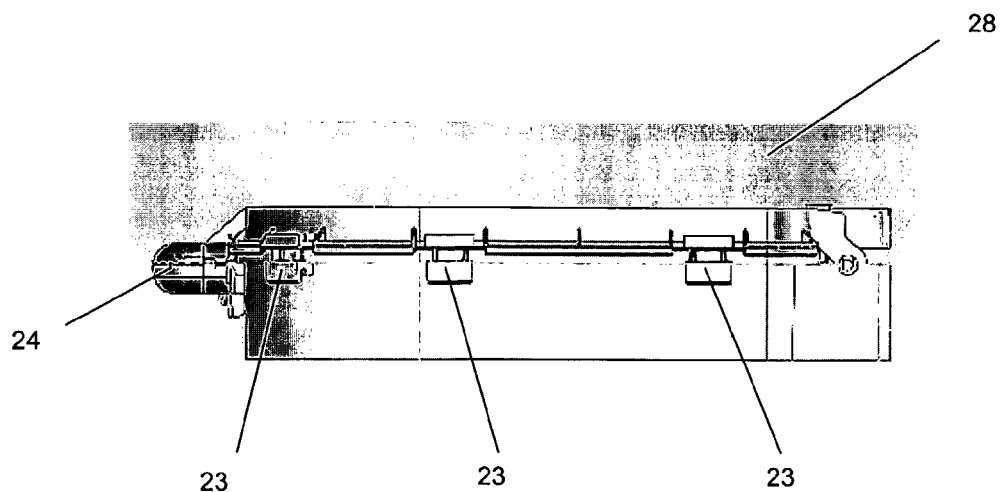
FIG. 14 is a side view of the sterilisation case 28.
Figure 15:
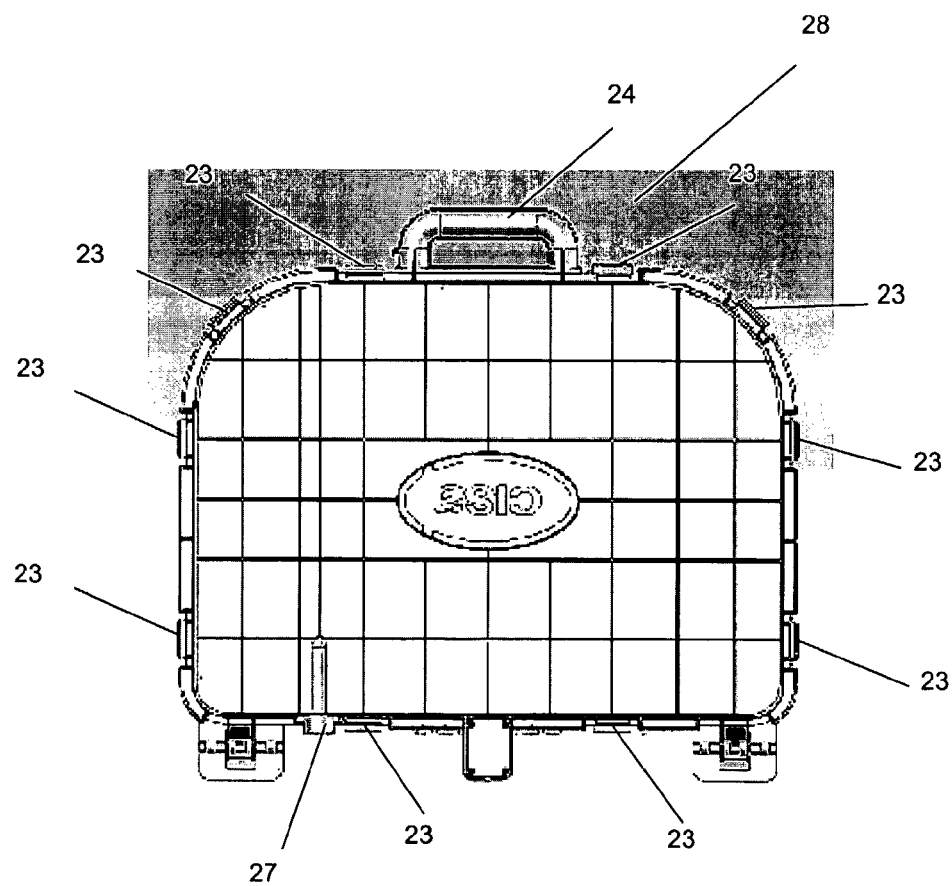
FIG. 15 is a top view of the sterilisation case 28.

As shown in FIGS. 13 to 15, the case 28 is built to assure the effectiveness of the treatment of the instrument and its preservation in a sterile environment. For this reason it has the following requirements: it is made of plastic material; it is light, strong and non deformable; it can be drained perfectly; its inner surface is rounded and smooth; it is compatible with its intended use; it has a sanitary construction; it is resistant to the substances used for the treatment; it has an inner shape that is suitable to house all the endoscopes by the different manufacturers; it is hermetically sealed by means of closures 23; its inner space is right for the endoscope and its capacity in liters is minimal; it is easily transportable with a handle 24; it has a display where the data of the content can be shown; it has the capability of maintaining the content sterile; it has quick couplings for connection to the washing and sterilising machine, 25a-f for the channels of the endoscope, 25g for the tightness test, 26a and 26b for injecting and discharging the liquid in the inner space of the case 28 and 27 for water level control.

Drying Cabinet

The drying cabinet has the function of drying the endoscope and preserving it in a sterile environment. Drying is achieved by safely heating the air that is injected into the channels of the endoscope inside the case by means of the connectors.

Work Cycle

The sequence of the various steps of the cycle is subordinated to the achievement of the specified conditions and of the set parameters. The steps are as follows:

Tightness Test:

Injection of compressed air into the sheath of the endoscope by means of the air pump MC and test of the pressure drop by means of pressure sensor TP7-1 and TP7-2. The injected air is filtered by the filter FA5.

Washing:

Injection of the detergent into the dosage tank C3 through the pump PP10 with dosage control through the measuring devices LE5 and LE6; loading the sterile water with the related detergent into the case 28 by means of the pumps MP-1, PD2-1 and MP-2, PD2-2; forced washing with the circulation pumps PP1-1, PP2-1, PP3-1, PP4-1, PP5-1, PP6-1 and PP1-2, PP2-2, PP3-2, PP4-2, PP5-2, PP6-2 for a time interval that depends on the detergent in use; discharge of the solution through the discharge valve PV5-1, PV5-2 and cleaning of the channels with compressed air filtered by the filter FA3.

Rinsing:

Loading sterile air into the case 28 by means of the pumps MP-1 and MP-2; forced rinsing with circulation pumps PP1-1, PP2-1, PP3-1, PP4-1, PP5-1, PP6-1 and PP1-2, PP2-2, PP3-2, PP4-2, PP5-2, PP6-2; discharging through the discharge valve PV5-1, PV5-2 and cleaning the channels with compressed air filtered by the filter FA3.

Sterilisation:

Preparation of the dosage of the peracetic acid and adazone (or of another sterilising compound) according to the following steps:

injection of the peracetic acid into the dosage tank C1 by means of the pump PP7, with dosage control by means of the measuring devices LE1 and LE2;

injection of the adazone into the dosage tank C2 by means of the pump PP9, with dosage control by means of the measuring devices LE3 and LE4;

loading sterile water with the related sterilising compound into the case 28 by means of the pumps MP-1, PD1-1, PD3-1 and MP-2, PD1-2, PD3-2; forced washing with the circulation pumps PP1-1, PP2-1, PP3-1, PP4-1, PP5-1, PP6-1 and PP1-2, PP2-2, PP3-2, PP4-2, PP5-2, PP6-2 for a time interval from 10 minutes to 40 minutes, variable according to the sterilising compound in use (sterilisation); discharge of the solution through the discharge valve PV5-1, PV5-2 and cleaning the channels with compressed air filtered by means of the filter FA3.

Rinsing:

Loading sterile water into the case 28 by means of the pump MP-1 and MP-2; forced rinsing with circulation pumps PP1-1, PP2-1, PP3-1, PP4-1, PP5-1, PP6-1 and PP1-2, PP2-2, PP3-2, PP4-2, PP5-2, PP6-2; discharge of the solution through the discharge valve PV5-1, PV5-2 and cleaning the channels with compressed air filtered by means of the filter FA3.

Alcoholisation:

Injection of alcohol into the channels through valve PV2-1 and PV2-2 by means of the pumps PP1-1, PP2-1, PP3-1, PP4-1, PP5-1, PP6-1 and PP1-2, PP2-2, PP3-2, PP4-2, PP5-2, PP6-2; injection of compressed air filtered by means of the filter FA3 into the channel and dilution of the alcohol; discharge of the residual solution.

Drying:

Drying takes place at the end of the cycle, preferably with injection of sterile air into the case and into the channels, but it can also be conducted subsequently in proper drying cabinet.

The invention claimed is:

1. A system for washing and sterilising endoscopes having multiple channels held by a sheath, the system comprising:
a case having a hermetic closure into which an endoscope is positioned, the case having an outlet connector for circulation;
a machine detachably connectable to the case, the machine comprising:
connectors having safety valves configured to connect with the multiple channels of the endoscope to inject liquids and gases for washing, sterilising, emptying and drying the multiple channels of the endoscope;
at least one connector having a safety valve configured to connect to the inner space of the case to inject liquids and gases for washing, sterilising, emptying and drying the inner space of the case;
a plurality of pumps, wherein a respective pump is connected to one of the multiple channels by a respective connector configured to connect with the multiple channels of the endoscope, and wherein a pump is connected to the inner space of the case by the at least one of the connectors configured to connect to the inner space of the case; and
a tightness tester configured to inject sterile air into an area of the endoscope inside the sheath through one of the connectors to verify tightness;
a device configured to control a water level inside the case, the device comprising a water level sensor;
wherein the case is configured to be detachable from the machine after a working cycle of the machine and configured so that the inner space of the case remains in sterile conditions when the case is detached from the machine.

2. The system of claim 1, wherein the machine is connected to more than one case and it is able to execute separate cycles for each case.

3. The system of claim 1, wherein the pumps are separated and are peristaltic pumps, the system further comprising:
a plurality of pressure transducers connected to the peristaltic pumps.

4. The system of claim 1, further comprising:
first and second water pre-filters;
a water filter;
a compressed air filter;
an intake filter; and
a loop configured for sterilising the water filter.

5. The system of claim 1, wherein the pumps circulate the liquid and the gases in the multiple channels of the endoscope and the inner space of the case.

6. The system of claim 1, wherein the pumps discharge the liquid and the gases from the multiple channels of the endoscope and the inner space of the case.

7. The system of claim 1, wherein the liquids comprise a detergent, a sterilising solution, sterile water and alcohol.

8. The system of claim 1, further comprising:
a drying cabinet.

9. A system for washing and cold sterilising an endoscope having multiple channels held by a sheath, the system comprising:
a case having an hermetic closure into which the endoscope is placed;
a machine detachably connected by means of multiple connectors fitted with safety valves to the case;
each respective channel of the endoscope connected to the machine by means of a respective connector;
an inner space of the case connected to the machine by an inlet connector and an outlet connector on the case for providing circulation to the machine;
the machine configured with an additional connector and the machine configured to verify the tightness of the region of the endoscope inside the sheath by injecting sterile air via the additional connector into a region of the endoscope inside the sheath;
the machine configured to inject washing and sterilisation liquids and/or the gases into the multiple channels of the endoscope for washing, emptying, and drying each of the channels;
the machine configured to inject washing and sterilisation liquids and/or the gases into the inner space of the case for washing, emptying, and drying the inner space of the case; and
the case configured to remain in a sterile condition upon being detached from the machine after a working cycle of the machine.

10. The system of claim 9 further comprising:
means for controlling the machine in a continuous and automatic cycle, the cycle comprising:
conducting a tightness test on the sheath of the endoscope by injecting sterile air into the region of the endoscope inside the sheath;
washing each channel of the endoscope by introducing detergents at ambient temperature, for time intervals;

rinsing each channel of the endoscope by introducing water into each channel of the endoscope;

sterilising each channel of the endoscope by introducing sterilising compounds at ambient temperature, into each channel of the endoscope, for time intervals;

rinsing each channel of the endoscope by introducing sterile water into each channel of the endoscope; and drying each channel of the endoscope by introducing sterile gases into each channel of the endoscope.

11. The system of claim 10 wherein the means for controlling the machine in a continuous and automatic cycle, further comprises the cycle comprising:

injecting a detergent into the case;

discharging the detergent from the case;

injecting sterile air into the case to rinse the;

discharging the sterile air from the case;

injecting a sterilising solution into the case;

discharging the sterilising solution from the case;

injecting sterile water into the case;

sensing a water level inside the case;

controlling a level of sterile water in the case using said sensed water level; and discharging the sterile water from the case.

12. The system of claim 11, wherein injecting of the detergent into the case comprises:

injecting a detergent including proteazone.

13. The system of claim 11, wherein injecting of the sterilising solution into the case comprises:

injecting a sterilising solution comprising peracetic acid and adazone.

* * * * *

UNITED STATES PATENT AND TRADEMARK OFFICE
CERTIFICATE OF CORRECTION

| | | |
|---|---|---|
| PATENT NO. | : 8,591,668 B2 | Page 1 of 1 |
| APPLICATION NO. | : 11/449605 | |
| DATED | : November 26, 2013 | |
| INVENTOR(S) | : Silvano Pieroni et al. | |

It is certified that error appears in the above-identified patent and that said Letters Patent is hereby corrected as shown below:

In the Claims:

- Col. 15, Claim 1, line 55: the phrase "the inner" should have been replaced with "an inner"
- Col. 17, Claim 11, line 15: the phrase "to rinse the;" should have been deleted and showing line 15 as "injecting sterile air into the case;"

Signed and Sealed this
Fifteenth Day of July, 2014

Michelle K. Lee
*Deputy Director of the United States Patent and Trademark Office*